United States Patent
Wong et al.

(10) Patent No.: US 6,455,095 B2
(45) Date of Patent: Sep. 24, 2002

(54) THERMOGENIC, APPETITE SUPPRESSING, GAS SUPPRESSING, COMPLETE LEGUME PROTEIN FORMULAE; THERMOBEAN™

(75) Inventors: Leonard J. Wong, San Antonio; Thomas S. Parker, Georgetown, both of TX (US)

(73) Assignee: ThermoBean L.P., Georgetown, TX (US)

( * ) Notice: Subject to any disclaimer, the term of this patent is extended or adjusted under 35 U.S.C. 154(b) by 0 days.

(21) Appl. No.: 09/870,404

(22) Filed: May 30, 2001

Related U.S. Application Data

(60) Provisional application No. 60/207,746, filed on May 30, 2000.

(51) Int. Cl.⁷ ................................................. A23L 1/20
(52) U.S. Cl. ........................... 426/634; 426/44; 426/46; 426/656; 426/804
(58) Field of Search ................................. 426/804, 634, 426/656, 46, 44

(56) References Cited

U.S. PATENT DOCUMENTS

| | | | | |
|---|---|---|---|---|
| 4,259,358 A | * | 3/1981 | Duthie | 426/46 |
| 4,431,737 A | * | 2/1984 | Olivieri et al. | 426/46 |
| 5,100,679 A | * | 3/1992 | Delru | 426/46 |
| 6,159,738 A | * | 12/2000 | Bell et al. | 424/439 |

* cited by examiner

*Primary Examiner*—Helen Pratt
(74) *Attorney, Agent, or Firm*—Jenkens & Gilchrist A Proffessional Corporation

(57) ABSTRACT

A dietary supplement for legume protein containing galactosidase, methionine, medium chain fatty acids or their derivatives, and optionally thermogenic additives, antioxidants, vitamins and spices. Improved legume protein is also provided, wherein the dietary supplement is already admixed with the legume protein. It may be formulated as a dried powder that can easily be reconstituted as refried beans, protein shakes, soups and the like. Alternatively, ready-to-eat foods may be prepared as described. A method of reducing body weight is also provided, the method being consuming at least a single serving of legume protein per day, wherein said legume protein is as described above. Methods of weight control, include avoiding the consumption of foods with a high glycemic index and consuming foods with a low glycemic index and also avoiding the consumption of foods that stimulate the appetite and consuming foods that satiate the appetite.

7 Claims, No Drawings

THERMOGENIC, APPETITE SUPPRESSING, GAS SUPPRESSING, COMPLETE LEGUME PROTEIN FORMULAE; THERMOBEAN™

CROSS REFERENCE TO RELATED APPLICATIONS

This application claims priority to a prior U.S. Provisional patent application, Ser. No. 60/207,746, filed May 30, 2000, entitled Thermogenic, Appetite Suppressing, Gas Suppressing, Complete Legume Protein Formulae, THERMOBEAN™.

FEDERALLY SPONSORED RESEARCH

Not applicable.

REFERENCE TO MICROFICHE APPENDIX

Not applicable.

FIELD OF THE INVENTION

The invention relates to diet plans that include legume proteins made nutritionally complete, and containing galactosidase, thermogenic compounds, and medium chain triglycerides. Antioxidants, polyphenols, proanthocyanin oligomers, vitamins and various other supplements may be included therein.

BACKGROUND OF THE INVENTION

In the past 3 decades, there were only a few states where greater than 15% of the total population were significantly overweight. In the past decade however, three quarters of all states in the union have become "fat" states. Amazingly and rather suddenly, the number of obese people in the U.S. has doubled in only the past few years. Obesity has become the second leading cause of preventable death (after smoking) in our part of the world. Doctors see 300,000 people die needlessly from its complications each year.

For years, nutritionists have taught that avoiding fat would prevent or at least reduce obesity. Although based on a worthy premise, the American low fat diet turned out to be a dismal failure. Very few people really commit to it. Probably only about 5% of Americans for whom the low-fat diet is recommended actually stay on it consistently for the long-term. To Doctor's surprise, many people actually gain weight as they switch from fatty to high starch foods which entice them to eat much more.

Even more disappointing is the lack of benefit for those with high cholesterol or heart disease. No study can directly prove that people on the diet feel better, live longer, or have less illness. In fact, studies showed that the diet doesn't even lower cholesterol (unless the patients also exercises). Even in instances where cholesterol was lowered, the "good" (HDL) cholesterol particles are lowered as much as the "bad" (LDL) type, resulting in no net benefit. When compared to a higher fat European-style diet, the results of the American diet were very disappointing. The "low-fat" diet was associated with up to 65% more heart attacks and related problems.

Looking back objectively, some reasons that the low-fat diets failed become apparent. Most people missed the flavor and texture of fat. They traded this for the sensuous pleasure of simple sugars. Sweet foods greatly whet the appetite, causing people to always have an unsatisfied desire for more. Many became rapidly addicted to the "sugar high" and fell victim to "sugar toxicity," often a prelude to diabetes. Massive weight gain and increasingly poor health followed.

Today, "protein diets" are exceedingly popular because high protein foods taste good, are satisfying to the appetite, and compliance is easier to maintain. Because of freedom from the "sugar cravings," most people do lose weight and are better able to keep the extra pounds off. Early findings show an actual improvement in the blood cholesterol particles. However, even with the great promise of the protein diets, there are still problems. Most of the highest protein foods are meat-based and contain high fat. Meats are objectionable to some persons. Further, high protein intake creates a high oxidative stress, which might in the long term be unhealthy.

Thus, a need exists for an inexpensive diet that does not stimulate the appetite or create sugar cravings, provides a nutritionally complete protein source, yet is palatable to all and does not have unnecessarily high fat levels. The invention described herein provides these and other benefits.

SUMMARY OF THE INVENTION

The invention is a dietary supplement for legume protein, that contains galactosidase, methionine, medium chain fatty acids or their derivatives, and optionally containing thermogenic additives. The supplement may also contain antioxidants, vitamins and spices.

In another embodiment, the invention is an improved legume protein, wherein legumes are improved by adding galactosidase, methionine, medium chain fatty acids and their derivatives, and optionally thermogenic additives. The improved legume protein may also include antioxidants and vitamins, including such grape seed, green tea, proanthocyanin oligomers and polyphenols. The legumes may also contain omega-3 fatty acids. The improved legume protein may be formulated as a dried powder, that can easily be reconstituted as refried beans, protein shakes, soups and the like.

In another embodiment, the invention is a method of reducing body weight, by consuming at least a single serving of legume protein per day, wherein said legume protein is fortified with galactosidase and methionine or is as described above. Methods of weight control, include avoiding the consumption of foods with a high glycemic index and consuming foods with a low glycemic index and also avoiding the consumption of foods that stimulate the appetite and consuming foods that satiate the appetite.

The invention in another embodiment relates to methods of manufacturing legume protein supplements as described above.

In one preferred embodiment for every 20 grams of legume protein there is provided 10–100 or 20–50 mg of methionine, 50–500 or 75–400 mg of medium chain triglycerides, 10–1000 or 50–100 mg of grape seed, and 100–5000 or 200–500 mg of green tea, 50–1000 or 75–100 mg of Vitamin B6, 10–1000 or 20–100 mcg of Vitamin B12, 100–1000 or 200–400 µg of folic acid and 50–5000 or 100–250 mg of Vitamin C and 50–5000 or 100–250 mg of flax seed.

In other embodiments, the invention is a method of reducing body weight, using the above products. A method of weight control by avoiding the consumption of foods with a high glycemic index and consuming foods with a low glycemic index or avoiding the consumption of foods that stimulate the appetite and consuming foods that satiate the appetite is also provided.

BRIEF DESCRIPTION OF THE DRAWINGS

Not applicable.

DESCRIPTION OF EMBODIMENTS OF THE INVENTION

Definitions

Alpha galactosidase—includes metabolically active galactosidases that can hydrolyze non-reducing terminal alpha 1-3,4,6 linked galactose from complex polysaccharides. Although several natural sources are available, recombinantly produced enzyme by Diversa Corp. (San Diego) is the currently preferred source.

Caffeine—includes trimethylxanthine or caffeine, its metabolically active derivatives and any other xanthine derivatives with stimulant effect similar to caffeine. Many stimulatory xanthines are chemically synthesizable, but a natural source is preferred.

Medium chain triglycerides—aka MCT—includes C6–C12 medium chain fatty acids, di- and triglycerides and other metabolizable derivatives. MCTs have a slightly lower calorie content than other fats, and they are more rapidly absorbed and burned as energy, resembling carbohydrate more than fat. Further, there is some evidence that they have some thermogenic effect and lower blood glucose levels. Natural (e.g., coconut oil, palm kernel oil, butter) or synthetic sources may be used.

Omega-3 fatty acids—includes the omega-3 fatty acids (linolenic acid, eicosapentaenoic acid, and docosahexaenoic acid) and metabolizable derivatives. May be obtained from flax, walnut, canola, soybeans, breast milk, fish or seafood. Many omega-3 fats are chemically synthesizable, but a natural source, such as flax, is preferred.

Proanthocyanin Oligomers—aka PCOs—an incompletely characterized set of bioflavonoids extracted from plants that include includes monomers and oligomers of proanthocyanin and anthocyanin and metabolically active derivatives. The PCO's are very powerful antioxidants. PCO's are preferably obtained from grape seed, preferably the green grape, but are obtainable from a variety of sources including other parts of the grape, blueberry, pine bark, and witch hazel. Many PCO's are chemically synthesizable, but a natural source is preferred.

Polyphenols—includes a variety of compounds not fully characterized from plants, especially green tea. Polyphenols exist as a series of chemicals called catechins, which include gallocatechin, epigallocatechin, epicatechin, epigallocatechin gallate, and epicatechin gallate and are also potent antioxidants and have cholesterol lowering activity. Other sources include red wine. Many polyphenols are chemically synthesizable, but a natural source is preferred.

The inventors have created a nutritionally complete dietary program or dietary supplement that is low fat, but has high levels nutritionally complete protein without added cholesterol, has significant amounts of fiber, and helps to control appetite. The formulation is called as "THERMOBEAN™" for short, and comprises legume protein, galactosidase to aid in starch digestion, amino acid supplements to ensure a nutritionally complete protein, medium chain fats, thermogenic supplements, antioxidants such as polyphenols and PCO's and other nutritional additives such as vitamins, spices, and the like.

In searching for a source of nutritionally complete, palatable, low fat protein, a variety of protein sources were considered and rejected. The protein powders sold in health food stores are expensive, very cumbersome and above all unnatural, unpleasant, and often poorly balanced. Red meats are pleasing to prepare and consume, but are expensive and contain high levels of fat and cholesterol. Eggs and dairy products contain a very well balanced protein, but are also very abundant in cholesterol and potentially harmful to many. Poultry products are abundant and relatively inexpensive, though some may consider them a bit bland. Proteins from fish and seafood are healthy and contain omega three fats that may help to prevent blood clots. However, fresh seafood is not always available, is expensive and may transmit disease. Instead, the inventors considered the use of a high protein vegetable—the legumes.

Legumes are a food family that contains peas, lentils, all varieties of beans, and even peanuts. This family is indeed, by far, the richest source of vegetable protein—even surpassing the protein content of some meats. Yet, this food contains virtually no fat and no cholesterol. A major advantage of legumes over animal protein is the abundance of dietary fiber. This has been found to reduce the incidence of certain cancers. Legumes have both kinds of beneficial fiber. Insoluble fiber aids digestion and bowel regularity, while soluble fiber helps buffer fluctuations in blood sugar and cholesterol. Beans actually contain more soluble fiber per serving than the highly touted oat bran!

Although legumes are the world's favorite protein source, they tend to be less frequently employed as a dietary staple in western countries due to the unpleasant side effects created by the presence of indigestible starches. The THERMOBEAN™ formula addresses this problem by providing an active enzyme to assist in the degradation of indigestible starches, thus minimizing or eliminating the production of gases produced by the fermentation of such starches in the intestine.

The second problem with the legume protein is that it is considered an incomplete protein, providing inadequate levels of the amino acid methionine. This is particularly problematic for diabetic patients because the body tends to eliminate the excess amino acids down to the level of the lowest amino acid available, and many nutritionists believe that elimination of these unmatched amino acids through the kidney may actually be harmful to those who have diabetic kidney disease. The high fiber and low fat content of legumes is ideal for all diabetics. Ironically however, those that have perhaps the worst complications may actually be advised to limit the "low biologic value" (incomplete) protein in beans. THERMOBEAN™ provides the solution, adding the missing amino acid methionine in sufficient amounts to make the legume protein fully utilizable. This converts the biologic value of the legume protein from "low" to "high." Tests of THERMOBEAN™ in patients with diabetic kidney disease have confirmed that there is no detriment in protein wastage.

Some foods have a known tendency to stimulate the appetite. These foods have one of three characteristics: They are either 1) sweet, 2) spicy (salty) or have a 3) high glycemic index. The "glycemic index" of food refers to the rate of release of simple sugar into the blood stream after the food is ingested. A high glycemic index food is to be avoided because it stimulates the production of insulin, which in excess can be detrimental. Some of the highest glycemic index foods include those with potato and corn starches, such as french fries, potato and corn chips, and corn syrup. The most powerful appetite stimulators have more than one appetite stimulating effect; for example the potato chip which is both salty and made of potato starch is almost impossible to resist. The legume proteins, in contrast, have a very low glycemic index.

Other foods, in contrast, "stymie" the desire to consume or inhibit the appetite. These foods often have better nutrient value and can be a great pleasure to consume. Such foods may stymie the appetite in a number of ways. Some stymie foods produce a large bulking effect that causes a full, satisfied sensation. Others activate hormonal release by the intestines that further suppress the desire to eat more. Yet others work on the brain's appetite control center to switch off the drive to eat. All stymie foods have a low glycemic index, thus avoiding the wide hormonal fluctuations that often trigger hunger or symptoms of "sugar toxicity." Legume proteins are considered a stymie food due to the low glycemic index and the high fiber content.

Fat is also a very good stymie food. A little fat in the intestinal tract slows down digestion and creates a full, satisfied sensation. Fat entering the blood stream triggers a number of hormonal reactions that again promote satiety. Fat also switches off the nerve centers that trigger hunger. The problem with fat is that it has over twice the amount of calories as sugar. In addition, it causes indigestion for many people and is very unhealthy for people with heart and vascular disease. Still, a small amount of fat can be beneficial, as seen above. The THERMOBEAN™ formulae combines the low glycemic index of legume protein with certain fatty acids that produce significant stymie effect. These fats include medium chain triglycerides, (which include the C6–C12 fats and their derivatives) as well.

The THERMOBEAN™ formulae also contains well known thermogenic supplements, including caffeine, chromium and ephedra extracts from the root of a plant known as *Ephedra sinica* or Ma Huang. Other thermogenic supplements may be incorporated, including certain spices such as the pepper spices.

Other ingredients may include the following: Naturally occurring omega-3 fatty acids, which stimulate thermogenesis and lower the glycemic index of foods. Flax contains significant levels of omega-3 fatty acids and is both anti-inflammatory and aids vascular health. Importantly, flax is quite hydrophilic and aids satiety via the intestinal bulking mechanism. ProanthoCyanin Oligomers (PCOs) are perhaps the most powerful natural free radical scavengers known and are found in their highest concentration in grape seed extract. Because high protein diets may be associated with high levels of oxidative stress, the addition of grape seed extract counters this with anti-oxidant activity, thereby further averting tissue degeneration. Green tea extract may provide the caffeine noted above, but is also a rich source of polyphenols which augment immune function and have been demonstrated in many world-wide studies to have cancer preventive properties.

Pyridoxine is a co-factor in many enzymatic reactions within the human body. Specifically, its value when added to the formulation is to improve the clearance of homocysteine via the enzyme, cystathionine B synthase. In a similar manner to pyridoxine, Vitamin B12 adds to the value of the formulation by shunting away homocysteine via a methyl transfer reaction. Folic acid likewise aids in the metabolic disposal of homocysteine (cycling with the L-Methionine contained in this formulation). The use of folic acid has been highly touted in prevention of various vascular diseases. Vitamin C functions to enhance the intestinal absorption of iron and other cations naturally occurring in legumes. Spices may be included for flavor.

EXAMPLE 1

THERMOBEAN™ Ingredients

The following ingredients are collected:

1) Alpha Galactosidase 100–500 Gal. Units.
2) L-Methionine 100–500 mg. Racemic mixtures of methionine may also be employed at twice the dosage.
3) Naturally occurring ephedra alkaloids 15–25 mg.
4) Naturally occurring caffeine 75–200 mg.
5) Medium chain triglycerides 250–500 mg.
7) Flaxseed powder 100–250 mg. Alternatively, flaxseed oil or other omega-3 fatty acid sources such as walnut, canola and soybean may be used. Fish oil is another source, but may detract from the flavor. Large amounts of flax seed may also detract from the flavor of the final product and are preferable avoided. Additional bulk may be additionally provided by other bulking agents, such as psyllium, bran, guar gum and the like.
8) Chromium Picolinate 100–25 mcg. Alternatively, other sources of chromium may be used, provided they are nontoxic, digestible and palatable.
9) Grape Seed Extract 10–100 mg.
10) Green Tea Extract 40–250 mg.
11) Vitamin B6 (Pyridoxine) 50–100 mg.
12) Vitamin B12 20–100 mcg
13) Folic Acid 100–400 mcg
14) Vitamin C 50–250 mg. Vitamins may be obtained from any convenient source, including natural extracts, and any biochemically effective derivative is acceptable.
15) Spices—Added to taste. Formulation may vary to provide a spice suitable for a particular legume preparation style.

EXAMPLE 2

THERMOBEAN™ Manufacture

Powered THERMOBEAN™ is prepared by mixing dried powder ingredients. The powdered mix is divided into single meal aliquots of about 3 g (intended for use with single servings of legume protein of about 50–100 g) and packaged for use. The mix can be sold separately or with pre-prepared ready-to-eat meals.

The THERMOBEAN™ powder can be added to a hot legume dish immediately before serving. Alternatively, a dried legume powder can be mixed with the THERMOBEAN™ mix and packaged as a protein shake, instant refried bean mix, legume soup mix, and the like, ready for reconstitution. The convenience of such ready-to-use meals is believed to be a significant advantage in assisting the consumer to maintain a weight control regime.

EXAMPLE 3

THERMOBEAN™ Use

A personal workbook cookbook, textbook and instructional manual are presented to consumers of the THERMOBEAN™ formula. This extensive material contains novel information for use of legumes in weight-loss programs.

The THERMOBEAN™ formulation is provided in a dosage to be employed with one meal. More than a single dose use per meal should be avoided and there should be at least 3 hours between servings. Consumers of THERMOBEAN™ should avoid excess use of stimulants, including caffeine (coffee, tea, or sodas) or the use of nasal decongestants. Persons with special health problems such as heart disease (especially heart palpitations, arrhythmias, or high blood pressure) or diabetes (especially with kidney problems) should consult their own personal physician before using the THERMOBEAN™ formulation. People who have anxiety, tremulousness, or insomnia should use caution. It is best to start with half a packet per meal for the first few days, gradually increasing to the full packet to avoid any side-effects.

A few persons should avoid this program altogether. These are people who have allergies to legume products. Also, it is strongly urged that pregnant and lactating women and people who use the older type of antidepressants known as MAO Inhibitors or who rely on high doses of nasal decongestants should not use the complete THERMOBEAN™ product as described above, but may follow the principles outlines here, omitting only the thermogenic components of the formulation. To aid in these special instances, THERMOBEAN™ may be formulated without the thermogenic components.

I Thermogenic Formula (alone)—29 obese subjects voluntarily consented to take part in a dose escalation study utilizing ephedrine and theophylline to assess the safety and efficacy of the independent and combined use of these agents in weight reduction. Each subject had previously failed to maintain desired body weight by diet and/or exercise which were not altered during the trial. The patients were typically considered "high-risk" individuals to take a thermogenic formula.

Each patient gave informed consent, underwent complete physical and laboratory exams, and graded exercise tests. Each then began taking ephedrine 6.25 mg 3 times daily with meals. After 1 week, unless limited by adverse effect, subjects were titrated to 12.5 mg and after 3 weeks to 18.5 mg TID, AC. During Phase I, each subject was randomized to receive either placebo or theophylline concomitantly in escalating does of 100 mg, 200 mg, and 300 mg daily on weeks 1, 2, and 3 respectively.

Phase II was identical in design except for cross-over in theophylline/placebo assignment. Subjects began week 1 of Phase II continuing their highest tolerated dosage of ephedrine, then continued to titrate as tolerated to a maximal dose of 25 mg TID. Each subject had weekly measurement of vital signs, weight, and interview for adverse experiences. At the conclusion of Phase I and Phase II, a physical examination was performed. Questionnaires were also collected at these visits.

Despite extending through holiday festivals, the use of the formulas resulted in 12.5 lb. average weight loss with no prescribed alteration of diet or exercise. Only one subject was unsuccessful at titrating to the highest dose level due to side-effect. There were no significant changes in vital signs and no serious adverse effects.

In accordance with previously published studies, ephedrine, augmented by methylxanthine, provides benefit for weight loss independent of diet or exercise alternations. No safety concerns were observed in a group of high-risk patients, each treated with up to 25 mg Ephedrine TID combined with up to 300 mg of theophylline.

II Legume Protein for Weight Loss—14 overweight volunteers followed a diet substituting legume protein for meat-based protein for 4–7 months. Each individual gave medical history and underwent physical exam and laboratory testing. Instructions were given for adherence to a low-glycemic diet. Weight was measured and counseling provided on a monthly basis. The majority of participants were men.

Weight loss correlated positively with compliance. Each subject lost weight on follow-up although variation was quite high (4–45 lbs.). Most subjects maintained at least 50% of the maximum weight loss from baseline until the study conclusion. The majority of subjects found the diet simple to follow and enjoyable.

Legume protein is a convenient, well-tolerated vehicle for long-term weight reduction.

III THERMOBEAN™ Liquid Formula—33 obese subjects who had previously been refractory to standard weight management techniques used a novel blend of natural substances as an additive to legumes in an evaluation of effects on weight loss. The study used 2 formulas in a cross-over design in 2 periods of 4 weeks each. The formulas were identical except one formula contained thermogenic compounds (ephedrine 22 mg/caffeine 80 mg and medium chain triglycerides) while the other formula contained none.

Each subject was given 2 hours of didactic instruction in 4 principles designated to aid weight reduction. These principles included:

1. Building legume protein into meals and snacks; recipes and techniques to inhibit gas.
2. Using low glycemic index foods to prevent "sugar toxicity" and cravings.
3. Avoiding foods that stimulate further intake, increasing foods that produce satiety.
4. Adding thermogenic elements to stimulate fat oxidation (randomized cross-over).

Group A was assigned from a random sample to receive the novel blend "A" which contained elements to enzymatically degrade complex polysaccharides thereby reducing intestinal. gas formation. The blend also contained L-methionine in an amount necessary to replace the deficiency of this compound (and cysteine) in legume protein. Group B was assigned to initially receive the same blend but additionally incorporating natural Ephedra alkaloids, caffeine, and also medium chain triglycerides in oil (blend "B"). Subject and examiners were blinded as to which blend contained active thermogenic elements. Subjects were examined at 2 week intervals and crossed over to the alternate blend at the end of 4 weeks.

The study was flawed by a manufacturing defect in the Blend B formula during the second phase of the study. Additionally, many subjects complained of the taste of Blend B and the drop-out rate was high. No patient experienced adverse changes in vital signs. There was no difference between the blends in any effect attributable to Ephedra/caffeine content. One patient discontinued after 2 days due to gas, four patients discontinued due to taste, and an additional 6 patients were lost to follow-up. In the remaining group, there was an average weight loss of 16 lbs. with an insignificant trend favoring Blend B. The findings were complicated by fewer subjects completing the second phase after cross-over to the flawed Blend B.

The liquid formula appeared effective and without medically significant side-effects in inducing weight loss in previously refractory obese patients. However, the formula was poorly tolerated due to taste problems and irregular batch consistency.

What is claimed is:

1. A dietary supplement for legume protein, comprising the following ingredients:
   1) galactosidase,
   2) methionine,
   3) medium chain fatty acids or their derivatives, and optionally containing
   4) thermogenic additives.

2. The dietary supplement of claim 1, further comprising antioxidants, vitamins and spices.

3. The dietary supplement of claim 2, wherein the antioxidants include proanthocyanin oligomers and polyphenols.

4. The dietary supplement of claim 3, wherein the antioxidants are derived from grape seed and green tea.

5. The dietary supplement of claim 4, further comprising flax seed.

6. The dietary supplement of claim 3, further comprising omega-3 fatty acids.

7. The dietary supplement of claim 1, wherein the galactosidase is alpha galactosidase, wherein the medium chain fatty acids are C6–C12 fatty acids or their derivatives, wherein the thermogenic additives include chromium, caffeine and ephedrine and their derivatives.

* * * * *